United States Patent
Zang et al.

(10) Patent No.: US 9,452,989 B2
(45) Date of Patent: Sep. 27, 2016

(54) COMPOUNDS, SENSORS, METHODS, AND SYSTEMS FOR DETECTING GAMMA RADIATION

(71) Applicant: University of Utah Research Foundation, Salt Lake City, UT (US)

(72) Inventors: Ling Zang, Salt Lake City, UT (US); Jimin Han, Salt Lake City, UT (US); Xu Miao, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 14/403,540

(22) PCT Filed: May 24, 2013

(86) PCT No.: PCT/US2013/042699
§ 371 (c)(1),
(2) Date: Nov. 24, 2014

(87) PCT Pub. No.: WO2013/177539
PCT Pub. Date: Nov. 28, 2013

(65) Prior Publication Data
US 2015/0118758 A1    Apr. 30, 2015

Related U.S. Application Data

(60) Provisional application No. 61/651,381, filed on May 24, 2012.

(51) Int. Cl.
*G01N 21/64* (2006.01)
*G01N 21/63* (2006.01)
(Continued)

(52) U.S. Cl.
CPC .......... *C07D 235/20* (2013.01); *C07D 235/02* (2013.01); *G01J 3/46* (2013.01);
(Continued)

(58) Field of Classification Search
CPC  C07D 235/20; C07D 235/04; C07D 235/02; C07D 235/00; G01J 3/46; G01J 3/00; G01T 1/10; G01T 1/02; G01T 1/00; G01N 21/6428; G01N 21/64; G01N 21/63; G01N 21/645; G01N 21/643; B82Y 15/00

USPC ....... 436/58, 57; 422/82.08, 82.02, 68.1, 50; 548/301.7, 300.1, 100, 1
See application file for complete search history.

(56) References Cited

U.S. PATENT DOCUMENTS

| | | |
|---|---|---|
| 3,691,384 A | 9/1972 | Robinson et al. |
| 3,790,389 A | 2/1974 | Heimsch et al. |

(Continued)

FOREIGN PATENT DOCUMENTS

| | | |
|---|---|---|
| EP | 1553449 A1 | 7/2005 |
| JP | H04271342 A | 9/1992 |

(Continued)

OTHER PUBLICATIONS

STN Search Report by STIC, obtained on Sep. 17, 2015, pp. 1-58.*

(Continued)

*Primary Examiner* — Christine T Mui
(74) *Attorney, Agent, or Firm* — Thorpe North & Western, LLP

(57) ABSTRACT

Methods, compositions, and systems for detecting gamma radiation is disclosed and described. A compound for detecting gamma radiation can comprise a conjugated imidazole having the following structure: [Formula I] where at least one of R1, R2, and R3 are conjugated organic groups. Additionally, the conjugated imidazole can be capable of reacting with a radical or ion formed by the reaction of gamma radiation with a radical generating component such as a halogen solvent to decrease a molar extinction coefficient of the conjugated imidazole in the visible light region or to quench fluorescence of the conjugated imidazole. As a sensor (100), a radiation detection indicator (108) can indicate the change in molar extinction coefficient or fluorescence of the conjugated imidazole material (120) upon exposure to gamma radiation.

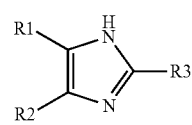

(I)

27 Claims, 5 Drawing Sheets

(51) Int. Cl.
  *B82Y 15/00* (2011.01)
  *G01J 3/46* (2006.01)
  *G01T 1/10* (2006.01)
  *C07D 235/20* (2006.01)
  *C07D 235/02* (2006.01)

(52) U.S. Cl.
  CPC ............... *G01T 1/10* (2013.01); *B82Y 15/00* (2013.01); *G01N 21/63* (2013.01); *G01N 21/64* (2013.01); *G01N 21/6428* (2013.01)

(56) References Cited

U.S. PATENT DOCUMENTS

| | | | |
|---|---|---|---|
| 3,801,320 | A | 4/1974 | Erickson |
| 3,897,255 | A | 7/1975 | Erickson |
| 3,899,334 | A | 8/1975 | Erickson |
| 3,904,411 | A | 9/1975 | Erickson et al. |
| 3,925,076 | A | 12/1975 | Heimsch et al. |
| 3,992,209 | A | 11/1976 | Erickson |
| 3,993,489 | A | 11/1976 | Heimsch et al. |
| 4,033,716 | A | 7/1977 | Defago et al. |
| 4,150,289 | A | 4/1979 | Rosauer et al. |
| 4,199,680 | A | 4/1980 | Moon |
| 4,234,674 | A | 11/1980 | Woodbrey et al. |
| 4,266,004 | A | 5/1981 | Kern |
| 4,271,262 | A | 6/1981 | Kern |
| 4,770,976 | A | 9/1988 | Loerzer et al. |
| 4,788,436 | A | 11/1988 | Koechner |
| 4,857,438 | A | 8/1989 | Loerzer et al. |
| 4,873,131 | A | 10/1989 | Kashima et al. |
| 4,910,149 | A | 3/1990 | Okube et al. |
| 5,008,539 | A | 4/1991 | Kirby |
| 5,064,603 | A | 11/1991 | Hurwitz et al. |
| 5,094,808 | A | 3/1992 | Meeh |
| 5,538,852 | A | 7/1996 | Carlson et al. |
| 6,021,240 | A | 2/2000 | Murphy et al. |
| 6,083,758 | A | 7/2000 | Imperiali et al. |
| 6,509,126 | B1 | 1/2003 | Whitesides et al. |
| 6,521,394 | B1 | 2/2003 | Whitesides et al. |
| 6,660,762 | B2 | 12/2003 | Sakalosky |
| 6,741,185 | B2 | 5/2004 | Shi et al. |
| 6,787,250 | B2 | 9/2004 | Shibuya et al. |
| 7,151,815 | B2 | 12/2006 | Ruddy et al. |
| 7,227,158 | B1 | 6/2007 | Patel et al. |
| 7,318,966 | B2 | 1/2008 | Tominaga et al. |
| 7,476,874 | B2 | 1/2009 | Patel |
| 7,510,699 | B2 | 3/2009 | Black et al. |
| 7,547,842 | B2 | 6/2009 | Wang |
| 7,989,781 | B2 | 8/2011 | Patel |
| 8,115,182 | B1 | 2/2012 | Patel |
| 8,133,474 | B2 | 3/2012 | Zhang et al. |
| 8,389,940 | B2 | 3/2013 | Barillon et al. |
| 2002/0160972 | A1 | 10/2002 | Cook et al. |
| 2005/0211978 | A1 | 9/2005 | Bu et al. |
| 2005/0271474 | A1 | 12/2005 | Smith et al. |
| 2009/0035783 | A1 | 2/2009 | Yang |
| 2009/0075362 | A1 | 3/2009 | Baumfalk et al. |
| 2009/0115623 | A1 | 5/2009 | Macpherson et al. |
| 2009/0128345 | A1 | 5/2009 | Patel |
| 2009/0155875 | A1 | 6/2009 | Berry et al. |
| 2009/0224176 | A1 | 9/2009 | Patel |
| 2010/0101955 | A1 | 4/2010 | Nocera et al. |
| 2010/0112545 | A1 | 5/2010 | Muralidharan et al. |
| 2010/0203649 | A1 | 8/2010 | Thrier |
| 2010/0228025 | A1 | 9/2010 | Cote et al. |
| 2010/0245121 | A1 | 9/2010 | Reed et al. |
| 2010/0302046 | A1 | 12/2010 | Karell |
| 2011/0035161 | A1 | 2/2011 | McFadden et al. |
| 2011/0081724 | A1 | 4/2011 | Swager et al. |
| 2011/0303850 | A1 | 12/2011 | Barillon et al. |

FOREIGN PATENT DOCUMENTS

| | | |
|---|---|---|
| JP | 2008/227347 A | 9/2008 |
| WO | WO 2007/047582 A3 | 4/2007 |

OTHER PUBLICATIONS

Yasui, Linda S. et al, Using Hoechst 33342 to Target Radioactivity to the Cell Nucleus, Radiation Research, 2007, vol. 167, pp. 167-175.*

Han, Ji-Min et al., Gamma Radiation induced self-assembly of fluorescent molecules into nanofiber: a stimuli-responseive sensing, J. Mater. Chem. C., 2015, vol. 3, pp. 4345-4351.*

Bhaumik C, Saha D, Das S, Baitalik S, et al. "Synthesis, structural characterization, photophysical, electrochemical, and anion-sensing studies of luminescent homo- and heteroleptic ruthenium(II) and osmium(II) complexes based on terpyridyl-imidazole ligand". *Inorg Chem.* (2011).

Bom V, Joulaeizadeh L, Beekman F, et al Real-time prompt γ monitoring in spot-scanning proton therapy using imaging through a knife-edge-shaped slit. *Phys Med Biol.* 2012.

Deng C, Niu Y, Peng Q, Qin A, Shuai Z, Tang BZ, et al. "Theoretical study of radiative and non-radiative decay processes in pyrazine derivatives". *J Chem Phys.* (2011).

Fiddler, M.N., et al. "Laser Spectroscopy for Atmospheric and Environmental Sensing." Sensors 9 12 (2009): 10447-512.

Haines, WE, and DR Latham. "Nonmetal Elements and Compounds." Analytical Chemistry 51 5 (1979): 231-38.

Heinze BC, Gamboa JR, Kim K, Song JY, Yoon JY, et al. "Microfluidic immunosensor with integrated liquid core waveguides for sensitive Mie scattering detection of avian influenza antigens in a real biological matrix". *Anal Bioanal Chem.* (2010).

Johnston, NS, et al. "Conference 8073A: Optical Sensors." *Connecting minds for global solutions*: 39. Apr. 18-20, 2011.

Juzenas, P., et al. "Quantum dots and nanoparticles for photodynamic and radiation therapies of cancer." Advanced drug delivery reviews 60 15 (2008): 1600-14.

Kawasaki, H., et al. "ph-Dependent Synthesis of Pepsin-Mediated Gold Nanoclusters with Blue Green and Red Fluorescent Emission." *Advanced Functional Materials* (2011).

Kim K, Gu MB, Kang DH, Park JW, Song IH, Jung HS, Suh KY, et al. "High-sensitivity detection of oxytetracycline using light scattering agglutination assay with aptasensor". *Electrophoresis.* (2010).

Kishikawa N, Wada M, Ohba Y, Nakashima K, Kuroda N, et al. "Highly sensitive and selective determination of 9,10-phenanthrenequinone in airborne particulates using high-performance liquid chromatography with pre-column derivatization and fluorescence detection". *J Chromatogr A.* (2004).

Kishikawa N, Wada M, Ohba Y, Nakashima K, Kuroda N, et al. "Highly sensitive and selective determination of 9,10-phenanthrenequinone in airborne particulates using high-performance liquid chromatography with pre-column derivatization and fluorescence detection." *J. Chromatogr A.* (2004).

Li YQ, Bricks JL, Resch-Genger U, Spieles M, Rettig W, et al. "Bifunctional charge transfer operated fluorescent probes with acceptor and donor receptors. 2. Bifunctional cation coordination behavior of biphenyl-type sensor molecules incorporating 2,2':6',2"-terpyridine acceptors". *J Phys Chem A.* (2006).

Li YQ, Bricks JL, Resch-Genger U, Spieles M, Rettig W, et al. "CT-operated bifunctional fluorescent probe based on a pretwisted donor-donor-biphenyl". *J Fluoresc.* (2006).

Lo, P.K., and M.S. Wong. "Extended Calix [4] arene-Based Receptors for Molecular Recognition and Sensing." Sensors 8 9 (2008): 5313-35

Resch-Genger U, Li YQ, Bricks JL, Kharlanov V, Rettig W, et al. "Bifunctional charge transfer operated fluorescent probes with acceptor and donor receptors. 1. Biphenyl-type sensor molecules with protonation-induced anti-energy gap rule behavior". *J Phys Chem A.* (2006).

(56) References Cited

OTHER PUBLICATIONS

Soper, S.A., L.B. McGown, and I.M. Warner. "Molecular fluorescence, phosphorescence, and chemiliminescence spectrometry." *Analytical Chemistry* 66 12 (1994): 428-44.

Strianese M, Varriale A, Staiano M, Pellecchia C, D'Auria S, et al. "Absorption into fluorescence. A method to sense biologically relevant gas molecules". *Nanoscale* (2011)

Yoshida, K., et al. "Fluorescence Sensing Behavior of Crystals of an Imidazole-Type Clathrate Host upon Contact with Gaseous Carboxylic Acids." Chemistry Letters 30 8 (2001): 808-09.

Zhao X, Suo Y, et al. Analysis of primary aromatic amines using precolumn derivatization by HPLC fluorescence detection and online MS identification. *J Sep Sci.* (2008).

Zhu, T.C. Real-Time Dosimetry and Optimization of Prostate Photodynamic Therapy: DTIC Document, 2006.

* cited by examiner

COMPOUNDS, SENSORS, METHODS, AND SYSTEMS FOR DETECTING GAMMA RADIATION

RELATED APPLICATION

This application claims the benefit of U.S. Provisional Application No. 61/651,381, filed May 24, 2012, entitled "Compounds, Sensors, Methods, and Systems for Detecting Gamma-Ray Radiation" and which is incorporated herein by reference.

GOVERNMENT INTEREST

This invention was made with government support under 2009-ST-108-LR0005 awarded by the U.S. Department of Homeland Security. The government has certain rights in the invention.

BACKGROUND OF THE INVENTION

Monitoring of gamma radiation is important for many applications, including nuclear power plants, medical radiology, and homeland security. Gamma radiation is particularly important to monitor and control because of its potential danger to the human body. There are two types of radiation which differ in their interaction with common chemical matter: ionizing and non-ionizing radiation. Ionizing radiation is considered more harmful because of its potential damage to DNA. Gamma radiation (also known as gamma rays) is a typical ionizing radiation (high energy photons, at a level of millions eV per photon), and research shows that the repair process for low dose gamma radiation exposure is much slower than for high dose exposure. Furthermore, the penetration depth of gamma radiation is much longer than $\alpha$ ($^4_2$He) and $\beta$ (electron, e) particles. This means that it is more difficult to shield gamma radiation than $\alpha$ ($^4_2$He) and $\beta$ (e) particles.

Gamma radiation is widely used in medical radiological therapy, the construction industry, and scientific research. For example, the medical treatment of tumors by gamma radiation (also referred to as "gamma knife") requires precise adjustment or calibration of the equipment on a daily basis to ensure that it emits the proper level, or dose, of gamma radiation. The tolerance of gamma radiation intensity levels in this type of application can be as low as 2%.

Scientists and engineers have developed several technologies to measure the dose of radiation, such as ion chambers, scintillation detectors, and semiconductor detectors. The detection mechanisms for ion chambers and semiconductor detectors are similar and based on the monitoring of ion pairs generated by the ionizing radiation. When the particles ($\alpha$ or $\beta$) or photons pass the sensor materials, charges (electron/hole pairs) will be generated due to the interaction of the particles with sensor materials. The collected current is then used as a signal output. Typically, one particle will generate ~30000 charged pairs and thus has a signal amplification effect. However, this mechanism suffers from low sensitivity in gas-based detectors and/or thermal noise at room temperature in semiconductor detectors. The scintillation detectors are based on fluorescence of the sensory material which is excited by radiation. But inorganic scintillation materials are based on single crystal material, which are costly to scale up. On the other hand, many previous organic scintillators do not have the energy resolution required for identification or quantification. Furthermore, the photon detectors used to detect light from the scintillator can suffer from external interference. For example, photomultiplier tubes (PMT) are sensitive to external magnetic fields, and silicon-based photodiodes are sensitive to the incident radiation itself. As such, accuracy of such devices can be unreliable.

Chemical sensors can provide advantages over the current instrument-based sensor systems, including ease of use, low cost, high adaptability for size miniaturization and combination or integration into current electronic instruments, high flexibility or conformability to be fabricated into various shapes or composite materials that are suited for different applications of radiation detection (e.g., nuclear security vs. radiology calibration in clinics), and unlimited options of molecular design and engineering so as to improve sensitivity. Although many types of chemical sensors have been developed, such chemical systems can only detect gamma radiation down a level of near 10 Gy, still several orders of magnitude higher than the level required for practical use in both nuclear security and medical areas. There is thus a technical gap between the research and development of chemical sensor systems and the real application of such systems.

SUMMARY OF THE INVENTION

A sensor for detecting gamma radiation can include a conjugated imidazole having the following structure:

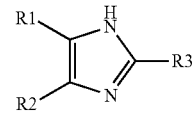

where at least one of R1, R2, and R3 are conjugated organic groups. The sensor can also include a radical generating component capable of reacting with gamma radiation to produce radicals, ions, or both. Additionally, the conjugated imidazole can be capable of reacting with the radicals or ions formed by the reaction of gamma radiation with the radical generating component, to decrease a molar extinction coefficient of the conjugated imidazole in the visible light region or to quench fluorescence of the conjugated imidazole. A radiation detection indicator can be operatively associated with the conjugated imidazole to indicate the change in molar extinction coefficient or fluorescence.

In another embodiment, a method for detecting gamma radiation can include placing a conjugated imidazole of the structure described above, with a radical generating component, in an area having gamma radiation. The method can further include identifying a color change associated with the decrease of the molar extinction coefficient of the conjugated imidazole or with the quench of the fluorescence of the conjugated imidazole. The change can be detected visually or with an electronic device such as a colorimeter or fluorimeter. Thus, qualitative and/or quantitative detection of gamma radiation can be provided.

In still another embodiment, a compound for detecting gamma radiation can include a conjugated imidazole with the structure described above.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

Understanding that these drawings merely depict exemplary embodiments of the present invention and they are, therefore, not to be considered limiting of its scope. It will be readily appreciated that the components of the present invention, as generally described and illustrated in the figures herein, could be arranged, sized, and designed in a wide variety of different configurations. Nonetheless, the invention will be described and explained with additional specificity and detail through the use of the accompanying drawings in which.

Figure 1A:
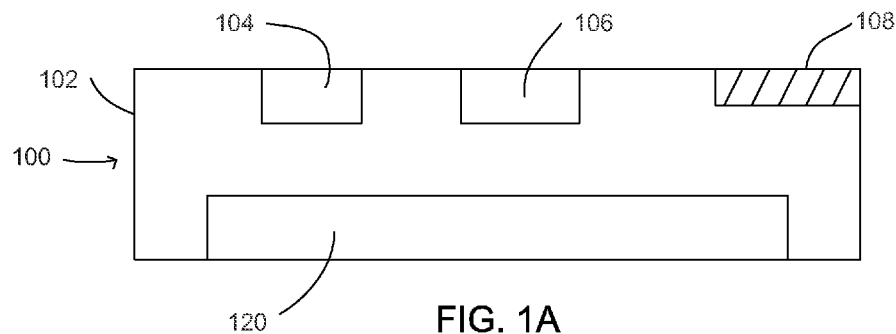
FIG. 1A-1C are cross sectional views of sensors in accordance with embodiments of the present invention.

Reference will now be made to the exemplary embodiments illustrated, and specific language will be used herein to describe the same. It will nevertheless be understood that no limitation of the scope of the invention is thereby intended.

DETAILED DESCRIPTION

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

It must be noted that, as used in this specification and the appended claims, the singular forms "a," "an," and "the" include plural referents unless the context clearly dictates otherwise. Thus, for example, reference to "a radical generating component" includes one or more of such materials, reference to "a conjugated moiety" includes reference to one or more of such groups, and reference to "an exposing step" includes reference to one or more of such steps.

DEFINITIONS

In describing and claiming the present invention, the following terminology will be used in accordance with the definitions set forth below.

As used herein, the term "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still contain such an item as long as there is no measurable effect thereof.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 10 to about 50" should be interpreted to include not only the explicitly recited values of about 10 to about 50, but also include individual values and sub-ranges within the indicated range. Thus, included in this numerical range are individual values such as 20, 30, and 40 and sub-ranges such as from 10-30, from 20-40, and from 30-50, etc. This same principle applies to ranges reciting only one numerical value. Furthermore, such an interpretation should apply regardless of the breadth of the range or the characteristics being described.

Detecting Gamma Radiation Using Conjugated Imidazoles.

A sensor for detecting gamma radiation can generally include a conjugated imidazole molecule, a radical generating component, and a radiation detection indicator. The radical generating component is a material capable of reacting with gamma radiation to produce radicals and/or ions. The conjugated imidazole can be selected from a series of t-conjugated imidazole based molecules that are capable of reacting with the radicals or ions to cause a change in a molecular extinction coefficient of the conjugated imidazole, causing a visible color change, or to quench the conjugated imidazole's fluorescence. The radiation detection indicator can indicate a change in the molar extinction coefficient or fluorescence of the conjugated imidazole. Thus, the sensor can detect gamma radiation by exhibiting a visible color change or a change in fluorescence of the conjugated imidazole.

The general structure of the conjugated imidazole is:

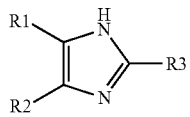

where at least one of R1, R2, and R3 are conjugated organic groups. In some cases each of R1, R2, and R3 are conjugated organic groups. Non-conjugated groups can be any chemical moiety which does not interfere with radiation detection as described herein. Such non-conjugated groups should not quench radicals (e.g. acids, bases, etc), should not be more reactive than imidazole, and should not trap or otherwise stabilize radicals (e.g. TEMPO, TEMPOL, nitronyl nitroxides, azephenylenyls, radicals from PTM and TTM, etc.), and the like. Non-limiting examples can include H, alkyls, ethylene glycols, cation-containing groups (e.g. pyridine cations, amine cations, phosphorous cations, etc.), anion-containing groups (e.g. carboxylic anions, sulfonic anions, sulfide anions, phosphate anions, etc.), and the like. Alkyl groups can be suitable for increasing solubility in hydrophobic solvents, while ethylene glycol groups can increase solubility in hydrophilic solvents.

Suitable conjugated organic groups can include, but are not limited to, vinyl, 1,3-butadienyl, ethynyl, carbonyl, 1,3-butadnyl, and combinations thereof. In some embodiments, R1, R2, and R3 can be conjugated aromatic groups. Some examples of suitable groups include five or six-membered rings, or combinations of multiple rings, with or without heteroatoms. By way of example, several suitable aromatic R-groups are shown below:

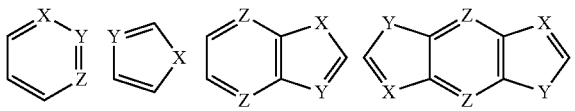

where X, Y, and Z are independently selected from C, N, S, O, Si, and P. Other suitable aromatic R-groups can include, but are not limited to, naphthalene, phenanthrene, carbazole, porphyrin, phthalocyanine, fluorene, and the like.

In some embodiments, R1 and R2 can from a single aromatic group. For example, R1 and R2 can form a single aromatic ring fused to the imidazole ring. In other embodiments, R1 and R2 can form a single group comprising multiple fused aromatic rings. Several examples of suitable fused aromatic groups are shown below:

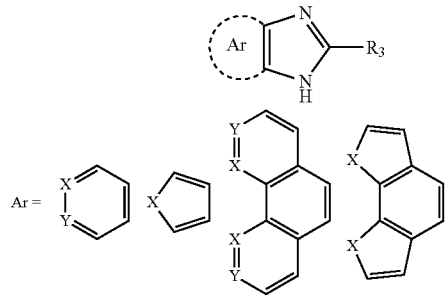

where X and Y are independently selected from C, N, S, O, Si, and P. Other suitable fused aromatic groups include naphthalene, phenanthrene, and the like.

In some embodiments, R3 can include a second imidazole group connected to the first imidazole group by a bridge group. The bridge group can be a suitable conjugated organic group, such as the R-groups listed above. Several examples of suitable bridge groups are shown below, referred to as R6:

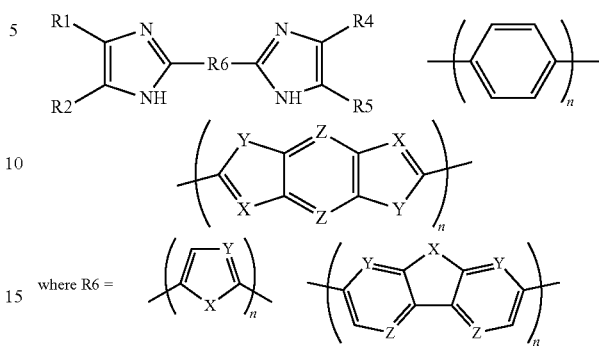

where R6 = where X, Y, and Z are independently chosen from C, N, S, O, Si, and P, and n is a positive integer. Thus, the bridge group can be a small molecule, oligomer, or a polymer. Accordingly, n can often range from 1 to 20, and in some cases up to about 100 as oligomeric groups, although polymeric structures where n is up to 1000 or more can also be suitable. R1, R2, R4, and R5 can be conjugated organic groups such as the R-groups described above, or they can form fused aromatic groups as described above. Bridge groups can also link more than two imidazole groups, for example, in a star pattern as shown below:

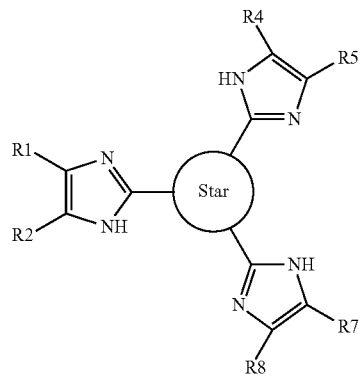

where R1, R2, R4, R5, R7, and R8 are conjugated organic R-groups such as those described above. These R-groups can also form fused aromatic groups as described above. The Star group can be a conjugated organic group capable of linking multiple imidazole groups. Several non-limiting examples of suitable Star groups are shown below:

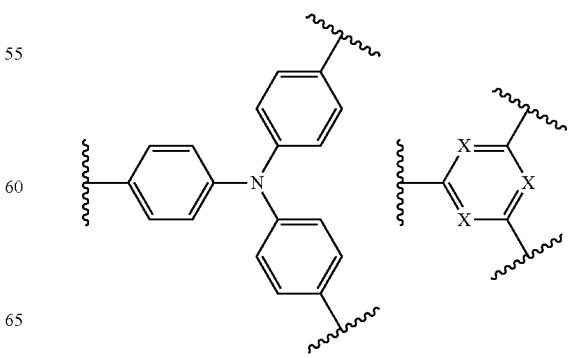

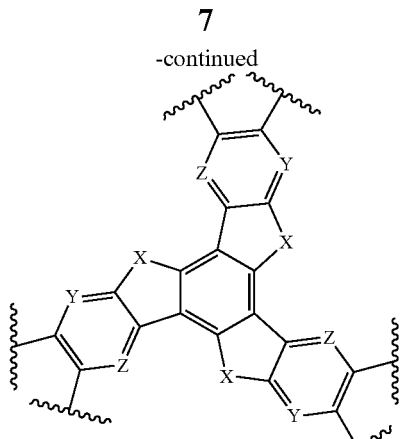

where X, Y, and Z are independently chosen from C, N, S, O, Si, and P.

In some embodiments, the conjugated imidazole can be selected from 4,4'-Bis(1H-phenanthro[9,10-d]imidazol-2-yl)phenyl (BPI-Ph); 4,4'-Bis(1H-phenanthro[9,10-d]imidazol-2-yl)biphenyl (BPI-BP); 1,4-bis(4,5-diphenyl-1H-imidazol-2-yl)benzene (BDPI-Ph); 4,4'-bis(4,5-diphenyl-1H-imidazol-2-yl)biphenyl (BDPI-BP); 2,2'-(9,9-bis(2-ethylhexyl)-9H-fluorene-2,7-diyl)bis(1H-phenanthro[9,10-d]imidazole) (BPI-Flu); 2,2'-(9-(2-ethylhexyl)-9H-carbazole-2,7-diyl)bis(1H-phenanthro[9,10-d]imidazole) (BPI-Cb); tris(4-(1H-phenanthro[9,10-d]imidazol-2-yl)phenyl)amine (PI-TPA); 2-phenyl-1H-phenanthro[9,10-d]imidazole (PI-Ph); 2,4,5-triphenyl-1H-imidazole (TPI); 4-(1H-phenanthro[9,10-d]imidazol-2-yl)-N,N-diphenylaniline (PI-DPA); N,N-dimethyl-4-(1H-phenanthro[9,10-d]imidazol-2-yl)aniline (PI-DMA); and the like. In a particular embodiment, the conjugated imidazole can have the following structure:

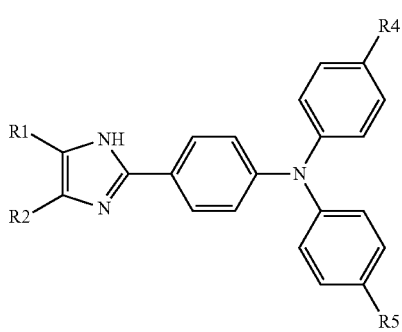

where R1 and R2 are conjugated organic groups such as the R-groups described above, and R4 and R5 are either conjugated organic groups or hydrogen. In one embodiment, R4 and R5 can be additional imidazole groups with attached R-groups.

The synthesis of the conjugated imidazole can be straightforward, taking only one step from commercially available precursors. For example, the synthesis of BPI-Ph (4,4'-Bis(1H-phenanthro[9,10-d]imidazol-2-yl)phenyl) and BPI-BP (4,4'-Bis(1H-phenanthro[9,10-d]imidazol-2-yl)biphenyl) is one example of synthesis of a conjugated imidazole. Synthesis of other conjugated imidazole molecules can be performed through similar processes.

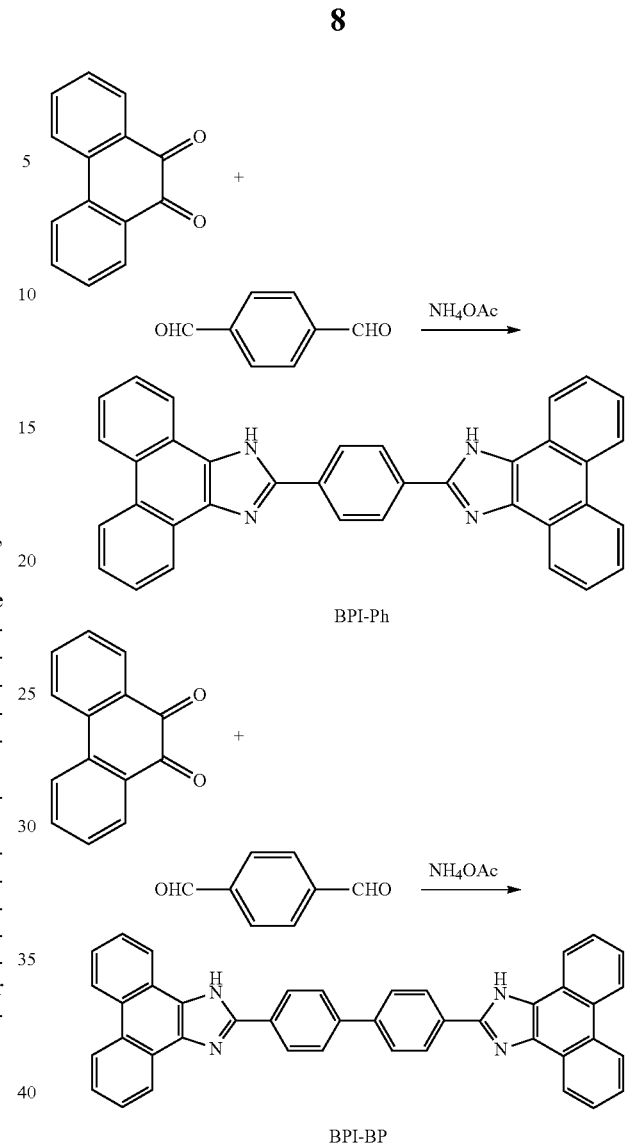

The R-groups of the conjugated imidazole molecules can be selected to provide various desired properties. For example, the absorption spectra of the conjugated imidazoles can be modified ranging from the ultraviolet to the visible region and their fluorescence spectra and intensity can be controlled via different substitutions. R-groups can be modified to improve solubility in different kinds of solvents, thus realize varied functions under different conditions. For example, long alkyl chains improve solubility in aliphatic solvents, while ethylene glycol chains make the molecules soluble in water. Additionally, with some R-groups, the conjugated imidazole molecules can be capable of coupling through π-π stacking. These conjugated imidazole molecules can thus be capable of one-dimensional self-assembly into nanofibrils. Such conjugated imidazoles can be used in solid-state sensors in the form of nanofibers or nanowires. In some embodiments, the conjugated imidazole can form a three-dimensional mass of nanofibers. In other embodiments, the conjugated imidazole can form a two-dimensional thin film. Furthermore, nanofibers made from other materials can be surface-modified with the conjugated imidazole. For example, chemical reactions can be used to attach functional groups at the end of the R-groups, which can react with existing nanofiber support material. Alternatively, donor-acceptor charge transfer complex can be used since most imidazole molecules are electron rich molecules, and can have strong interactions with electron deficient nanofibers, such as PDI molecules.

Generally, the conjugated imidazole can be selected from π-conjugated imidazole based molecules that are capable of reacting with the radicals or ions to cause a change in the conjugated imidazole's molecular extinction coefficient, causing a visible color change, or to quench the fluorescence of the conjugated imidazole. Many of the conjugated imidazoles described above can fluoresce under ultraviolet light and display a change in fluorescence or a visible color change when exposed to radicals or ions formed by gamma radiation. However, a conjugated imidazole on its own can require large doses of radiation to form sufficient radicals or ions to effect a detectable change in its fluorescence or color. Therefore, a radical generating component can be added to supply the conjugated imidazole with more radicals and ions.

The radical generating component can be capable of reacting with gamma radiation to produce radicals and ions that can then react with the conjugated imidazole. Typically, the radical generating components can be provided in copious excess (e.g. 1e6 or more in solution and effectively covering a surface when a nanofiber coating or think film). In some embodiments, the radical generating component can include a halogen solvent. Halogen solvents have been found to be effective at producing radicals and ions when exposed to gamma radiation. Without being bound to a particular mechanism, it is believed that gamma radiation causes the halogen solvent molecule to split into free radicals. Some free radicals recombine to form stable products, while others attack the conjugated imidazole molecules. It is believed that radicals attack at the imidazole site, altering the conjugation of the molecule and thus lowering its molar extinction coefficient or quenching its fluorescence. Additionally, with some halogen solvents the free radicals can recombine to form ions, such as protons. The ions can also react with the imidazole site to change the conjugated imidazole molecule's molar extinction coefficient and quench fluorescence.

In one specific embodiment the radical generating component can be chloroform and the conjugated imidazole can be BPI-Ph. Again, without being limited to a particular mechanism, it is believed that gamma radiation splits the chloroform molecules into free radicals. The chloroform initially splits into the primary radicals .CHCl$_2$ and .Cl. These can recombine into stable products or into secondary radicals .CCl$_3$ and .H. Any of these radicals can react with BPI-Ph as shown below:

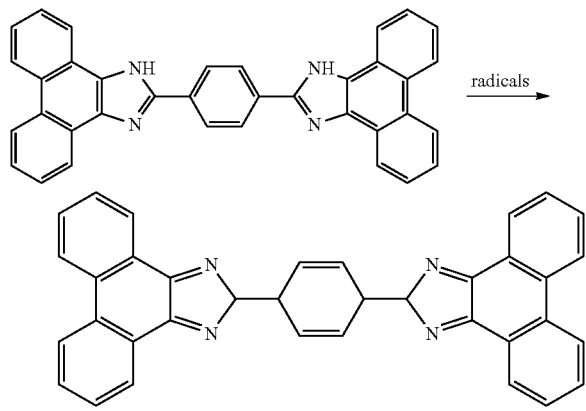

The radicals can also recombine to form HCl, which produces H$^+$ and Cl$^-$ ions. It is believed that the H$^+$ ions react with the imidazole site as shown below:

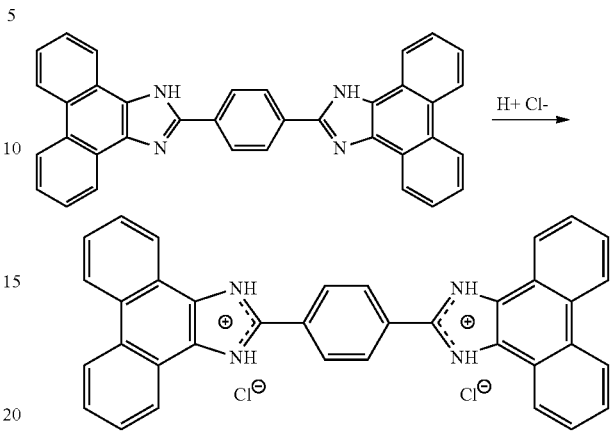

In many embodiments, the radical and ion mechanisms can both occur simultaneously. In some situations it may be preferred to favor one mechanism over the other. For example, the halogen solvent can produce a large amount of radicals, and therefore the radical mechanism can allow for better sensitivity. On the other hand, the ions can be easier to control and detect, which can allow for better selectivity, i.e. differentiating between gamma radiation and other types of radiation. The radical mechanism can be encouraged by extending the lifetime of the radicals. This can be accomplished by keeping the sensor in high vacuum, purging the sensor with Argon, and/or adding initiators. The initiators can include molecules that produce radicals, extend the lifetime of radicals, propagate radicals, and/or kinetically harvest radicals. Non-limiting examples of initiators include benzil, benzyl bromide, benzoyl peroxide, azobisisobutyronitrile (AIBN), tert-butyl hydroperoxide, cyclohexanone peroxide, 1,1'-azobis(cyclohexanecarbonitrile) (ABCN), acetone peroxide, 4,4'-azobis(4-cyanopentanoic acid), azobisisobutyronitrile, benzoyl peroxide, di-tert-butyl peroxide, methyl ethyl ketone peroxide, potassium persulfate, tributyltin hydride, and combinations thereof.

Furthermore, high-Z elements can be added to act as gamma radiation receivers. High-Z elements can absorb more radiation than smaller elements. The energy captured by the high-Z elements can be transferred to the halogen solvent to generate more radicals. For example, the radical generating material can include a molecule modified with a high Z-element (e.g. organic molecules containing a heavy element of atomic number 49 or greater, such as triphenylbismuth, diiodobenzene, or mixtures thereof. In embodiments where the ion mechanism is preferred, the radicals formed by the gamma radiation can be induced into specific cations and anions. This can be accomplished by adding alcohol or ether compounds (e.g. producing H$^+$ and alcohol$^-$ or H$^+$ and ether peroxide$^-$). Non-limiting examples of suitable alcohols and ethers can include methanol, ethanol, propanol, phenol, ethyl ether, tetrahydrofuran, dioxane, and the like.

In some embodiments the sensor can include a liquid solution with the conjugated imidazole dissolved in a halogen solvent. Various concentrations of the conjugated imidazole can be used. Concentrations of $10^{-7}$ to $10^{-4}$ mol/L have been found to be effective for some combinations of conjugated imidazoles and halogen solvents. Concentrations of $10^{-6}$ to $10^{-5}$ mol/L can particularly be effective with some combinations. Further, many halogen solvents can be suitable for use in a gamma radiation sensor. Examples of suitable halogen solvents include chloroform, dichloromethane, trichloroethylene, perchloroethylene, bromoform, diiodomethane, 1,2-dichloroethane, 1,1,1,2-tetrachloroethane, dibromomethane, and combinations thereof.

In further embodiments the conjugated imidazole and the halogen solvent can be present in a gel. The gel can generally be formed from a liquid solution surrounding a three-dimensional cross-linked network within the liquid. In some embodiments the three-dimensional network in the gel can comprise nanofibers of the conjugated imidazole.

In other embodiments, the radical generating component can include a radical generating polymer. Examples of suitable radical generating polymers include polymethylmethacrylate, polyolefinsulfone, polypropylene, 2-methyl nylon-3, and mixtures thereof. Radical generating polymers can be particularly suitable for embodiments wherein the conjugated imidazole has a nanofiber or thin film morphology. Nanofibers comprising the conjugated imidazole can be coated with a radical generating polymer. Gamma radiation can strike the radical generating polymer coating to produce radicals, which then diffuse to the conjugated imidazole nanofiber. Similarly, in thin film embodiments, a thin layer of radical generating polymer can be deposited over a thin layer of the conjugated imidazole. Radicals from the polymer layer can diffuse into the conjugated imidazole layer and react with the conjugated imidazole.

Generally, in some embodiments the conjugated imidazole can be present in a porous hydrophilic material. This porous hydrophilic material can include the conjugated imidazole in nanofiber or thin film morphologies as described above. In a particular embodiment including a nanofiber morphology, the porous hydrophilic material can comprise a cellulose fibril material. In other embodiments, the porous hydrophilic material can comprise nanofibers surface-modified with the conjugated imidazole. In each of these embodiments, a radical generating polymer can be added as the radical generating component.

Generally, the conjugated imidazoles can be directly bonded to a substrate through coating or other methods. A surface coating or binding can be performed through electrostatic interaction or hydrogen bonding between the conjugate imidazole and the surface of the substrate including —OH, —COOH or any other moieties available on the surface. Additionally, direct dispersion of a conjugated imidazole solution into a porous matrix (e.g., filter paper or silica gel) can be performed to associate the conjugated imidazoles with a substrate.

Generally, the porous hydrophilic material can be fabricated by depositing large numbers of nanofibers onto a substrate to form the thin film, where the nanofiber is surface-modified with the conjugated imidazoles. Non-limiting examples of such materials can be cellulosic paper, filtration paper, silica gel, polymer film, woven polymer, and the like. Typical hydrophilic or water soluble polymer materials can be commercially available from Dow, including but not limited to, CELLOSIZE® hydroxyethylcellulose (HEC), ETHOCEL® ethylcellulose polymers, KYTAMER® PC polymers, METHOCEL® cellulose ethers, POLYOX® water soluble resins, and the like. In one aspect, a porous silica gel can have greater than 1000 $m^2/g$ surface area. In another aspect, these substrates can be substantially transparent. In one embodiment, transparent silica-gel films that possess highly porous structure can be used.

One non-limiting example of a substrate preparation is a silica gel made from hydrolysis of tetramethoxysilane in the presence of cationic surfactants. The pre-matured gel solution (or emulsion) thus prepared is suited for spin-coating onto a flat substrate such as glass that is desirable for optical sensing. Briefly, tetramethoxysilane can be hydrolyzed in an acidic aqueous solution (tetramethoxysilane:water controlled at 1:10) for about one hour. Due to the substoichiometric amount of water, only partial hydrolysis will be obtained, leading to formation of a homogeneous solution. To this solution can be added alkyltrimethylammonium chloride, a surfactant used as template for forming the porous structure. After reacting under ambient condition for certain amount of time, the solution thus obtained can be spin-coated onto a glass slide, followed by drying in air to allow evaporation of solvent and condensation of the silica. Transparent thin film will eventually be formed on the substrate. Depending on the spin speed, films of different thicknesses, ranging from a few microns down to submicron, can be obtained.

The radical generating polymer can further include initiators and/or high-Z elements as described above, to alter or control the mechanism of reaction. For example, the radical generating polymer can be mixed with any of the initiators described above, or a molecule modified with a high Z-element, such as triphenylbismuth, diiodobenzene, or mixtures thereof. The radical generating polymer can also be mixed with ion inducers such as alcohols or ethers as described above. In some thin film embodiments, a molecule modified with a high-Z element, such as triphenylbismuth, can be used alone as the radical generating component without any radical generating polymer.

The conjugated imidazoles of the sensor can be used to detect gamma radiation by exhibiting a decrease, or quenching, of their fluorescence when they react with radicals and/or ions formed by gamma radiation. Depending on the sensitivity of the sensor incorporating the conjugated imidazole and the dose of gamma radiation, the fluorescence quenching can be a substantially complete quenching or a partial quenching. For example, a sample of conjugated imidazole that is fluorescing under ultraviolet light can go completely dark if it is completely quenched, or the sample can be slightly dimmed if it is only partially quenched. By correlating levels of quenching with radiation doses, it is possible for a sensor incorporating the conjugated imidazole to detect and quantify radiation doses over a wide range.

A sensor incorporating conjugated imidazoles and radical generating components as described above can have a very high sensitivity to gamma radiation. In many embodiments, the lower detection limit using this method can be between about $10^{-6}$ Gy and about 10 Gy. More particularly, in many cases the lower detection limit can be between about 0.001 Gy and about 1 Gy. The lower detection limit is the lowest level of radiation that will produce an observable and statistically significant change in the molar extinction coefficient or fluorescence of the conjugated imidazole. Various modifications to the sensor can increase its sensitivity. As explained above, the radical reaction mechanism can be encouraged by adding initiators and high-Z elements, thereby increasing sensitivity.

A significant increase in sensitivity can also be achieved by forming the conjugated imidazole in a nanofiber morphology. This increased sensitivity is due to interfacial charge transfer between conjugated imidazole molecules. When light is absorbed by the nanofiber, it creates an electron-hole pair, or an exiton. The exiton can freely diffuse throughout the nanofiber structure. Ordinarily, the electron-hole pair would eventually recombine, emitting light, or fluorescence. However, when the exiton meets a molecule of conjugated imidazole that has already reacted with a radical or ion, the electron transfers to that molecule instead of recombining to produce fluorescence. The long-range, one-dimensional molecular arrangement of the nanofibers allows the excitons to diffuse quickly to the quenching sites. This enables amplified fluorescence quenching by trace amounts of the reacted conjugated imidazole. Thus a sensor with the conjugated imidazole in a nanofiber morphology can generally have a higher sensitivity than with conjugated imidazole dissolved in a halogen solvent, because molecular diffusion in the solution occurs more slowly than diffusion in the nanofiber. Amplification of fluorescence quenching can also occur in a gel, if the three-dimensional matrix within the gel includes nanofibers that allow diffusion of exitons. Similarly, amplification of fluorescence quenching can occur in a thin film, although it would dominantly allow for diffusion in two dimensions instead of three.

With the above in mind, FIG. 1A shows a sensor 100 according to one embodiment. The sensor 100 includes a housing 102 enclosing liquid solution 120 of a conjugated imidazole and a radical generating component. As explained above, in some embodiments the conjugated imidazole can be dissolved in a halogen solvent, making a liquid solution. Also, the liquid solution 120 can contain additional optional materials such as initiators, molecules modified with high-Z elements, or ion inducers such as alcohols or ethers. A similar structure to the one shown in FIG. 1A can be used with a gel in place of the liquid solution 120 of conjugated imidazole and halogen solvent.

An optional light source 104 can be operatively associated with the liquid solution 120 containing the conjugated imidazole. As shown in FIG. 1A, the light source 104 can be located near the conjugated imidazole so as to shine light on the conjugated imidazole. Depending on the embodiment, the light source 104 can be an ultraviolet light source that excites the conjugated imidazole to fluorescence, or a visible light source that provides light sufficient to allow visual inspect of color of the conjugated imidazole.

A radiation detection indicator 106 can also be operatively associated with the conjugated imidazole. As shown in FIG. 1A, the radiation detection indicator 106 can be located near the conjugated imidazole so that a change in fluorescence or color of the conjugated imidazole is observable at the radiation detection indicator. In embodiments involving a change in fluorescence, the radiation detection indicator can be a fluorimeter configured to detect changes in the intensity of light emitted by fluorescence of the conjugated imidazole. In embodiments involving a decrease in the molar extinction coefficient of the conjugated imidazole, the radiation detection indicator can be a colorimeter configured to detect changes in color. The colorimeter can be any suitable colorimeter. Non-limiting examples of suitable colorimeters can include a commercial photon detector or portable colorimeter, such as those commercially available from Kittiwake and Preiser Scientific. Also, in other embodiments the radiation detection indicator can be a simple window to allow a human user to visually observe a change in fluorescence or color of the conjugated imidazole. Thus, the indicator can provide a simple 'yes' or 'no' signal that a given radiation threshold is met.

The sensor 100 can also include an electronic readout 108. The electronic readout 108 can be electronically connected to the radiation detection indicator 106 and configured to receive information from the radiation detection indicator 106 and communicate that information to a user. In some embodiments, the electronic readout can include a digital or analog display configured to show quantitative levels of detected radiation. In other embodiments the electronic readout 108 can be a visual or auditory signal such as a light or sound that is activated when a threshold level of radiation is detected. In yet other embodiments, the electronic readout 108 can be an interface that allows the sensor to connect to another external device for analyzing and displaying information about the level of detected radiation. External devices can include, but are not limited to, handheld computing devices, laptop computers, desktop computers, and the like.

The housing 102 can be in any convenient configuration. One will appreciate that gamma radiation can easily penetrate many types of material, so the sensor can include a closed housing 102 without affecting sensitivity to gamma radiation. In many embodiments the housing is a case made from plastic or metal. The housing does not need to be fully enclosed, although an enclosed housing can be useful to protect the elements inside from damage or dust. Furthermore, in some embodiments an enclosed housing can be used to keep the conjugated imidazole under vacuum or an inert atmosphere such as argon. Alternatively, gamma radiation levels can be a function of particulate containing gas flows such that a gas flow path can be directed across the corresponding detection material. Accordingly, a gas flow inlet and gas flow outlet can optionally be provided in the housing.

Figure 1B:
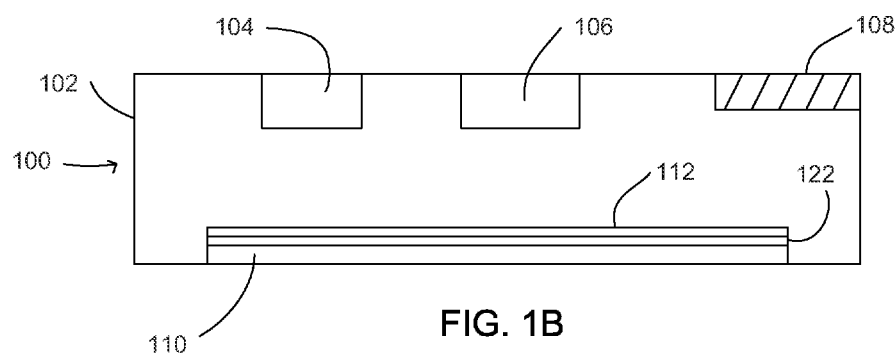

Another embodiment, shown in FIG. 1B, includes a thin film comprising a layer of conjugated imidazole 122 and a layer of radical generating polymer 112 deposited on a substrate 110. As explained above, the radical generating polymer 112 can also include initiators, high-Z elements, and ion inducers if desired. Gamma radiation can strike the layer of radical generating polymer 112 to produce radicals and ions, which then diffuse into the layer of conjugated imidazole 122. Typically, such think films can have a thickness from about 100 nm to about 100 mm, although other thicknesses can be suitable.

Figure 1C:
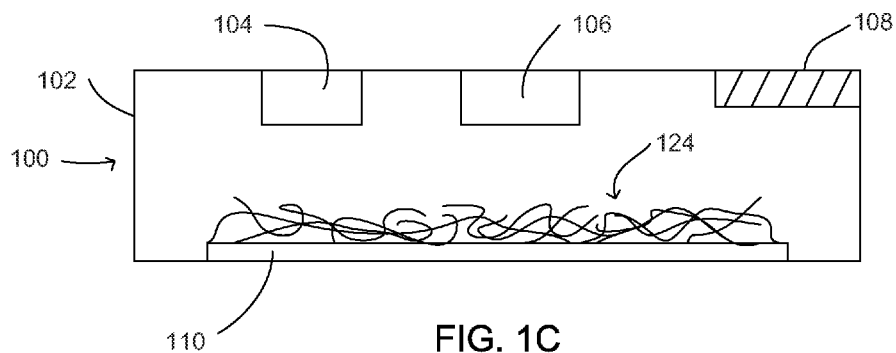

A further embodiment is shown in FIG. 1C, in which a mass of nanofibers 124 is deposited on a substrate 110. The nanofibers 124 can include the conjugated imidazole and a radical generating polymer. As explained above, gamma radiation can strike a coating layer of radical generating polymer, producing radicals which diffuse to the conjugated imidazole in the nanofibers. This embodiment can provide amplification of fluorescence quenching because diffusion through the nanofibers is faster than in a liquid solution.

Figure 2:
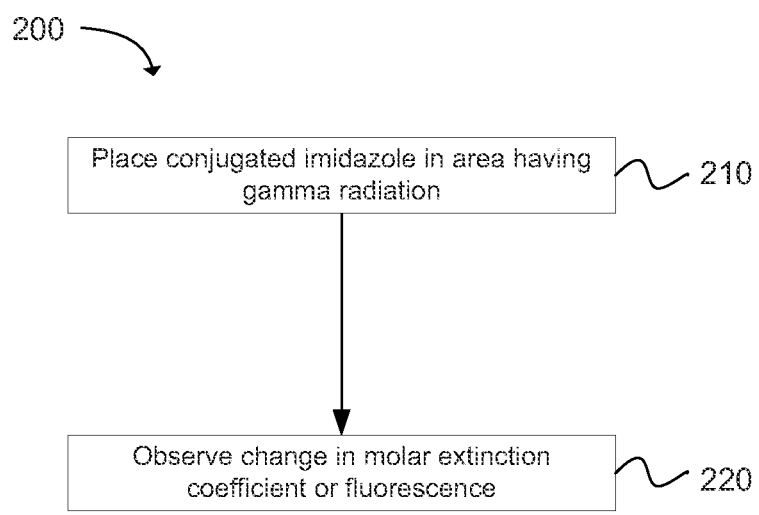
FIG. 2 is a flowchart showing a method for detecting gamma radiation in accordance with an embodiment of the present invention.

As shown in FIG. 2, a method 200 is also disclosed for detecting gamma radiation. As shown in step 210, a conjugated imidazole and a radical generating component of the types described above are placed into an area suspected of having gamma radiation. In step 220, changes are observed in either the molar extinction coefficient (through a visible color change) or the fluorescence of the conjugated imidazole. In some embodiments, the change can be observed directly by visual inspection. In other embodiments, the change is observed through an electronic detector such as a colorimeter or fluorimeter.

This method can be used to detect gamma radiation at low levels such that low detection limits can be reached. In many embodiments, the lower detection limit using this method can be at least between about 0.01 Gy and about 10 Gy, although lower limits may be reached by careful selection of materials and sensor configuration. More particularly, in many cases the lower detection limit can be between about 0.1 Gy and about 1 Gy. The lower detection limit is the lowest level of radiation that will produce an observable and statistically significant change in the molar extinction coefficient or fluorescence of the conjugated imidazole.

Although such methods can be desirable for use in security screening and threat detection, this method can also be effectively used in medical applications where a three-dimensional profile of radiation dosage is required. For example, a three-dimensional material incorporating the conjugated imidazoles disclosed herein can provide readings of radiation dosages received throughout a three-dimensional space at a very high level of sensitivity. This can be useful for routine calibration of medical instruments for radiation therapy applications. Medical treatment by photon radiation for tumors can require periodic precise verification and adjustment of radiation dose output, and the tolerance of radiation dose output can be as low as 2%. The disclosed method can be used to create a three-dimensional map of radiation dosage with a resolution in the sub-millimeter range and to calibrate radiation dosage equipment. In addition, there are other situations in which it would be useful to verify radiation dosage such as in vivo patient dose monitoring and small field dosimetry for stereotactic radiosurgery (SRS).

In addition, the observed response to gamma radiation is specific, proving high selectivity over other types of radiation, e.g., $\alpha$ ($^4_2$He) and $\beta$ (e) particles. The ease of modification of the side chain and $\pi$-conjugated structure of the present compounds can provide facile solubility adjustment and enhanced gamma-ray photosensitivity, making it feasible to develop chemical based sensors with detection limits suited for practical application in medical and clinical monitoring of gamma radiation, as well as nuclear security screening. Additionally, this series of molecules can also be fabricated into nanofibril materials that can be transformed into three-dimensional porous sensor materials through surface deposition and interface engineering. The fabrication methods can be developed based on both "top-down" patterning and "bottom-up" self-assembly methods. These three-dimensional materials can be useful in medical applications as described above.

Examples

Figure 3:
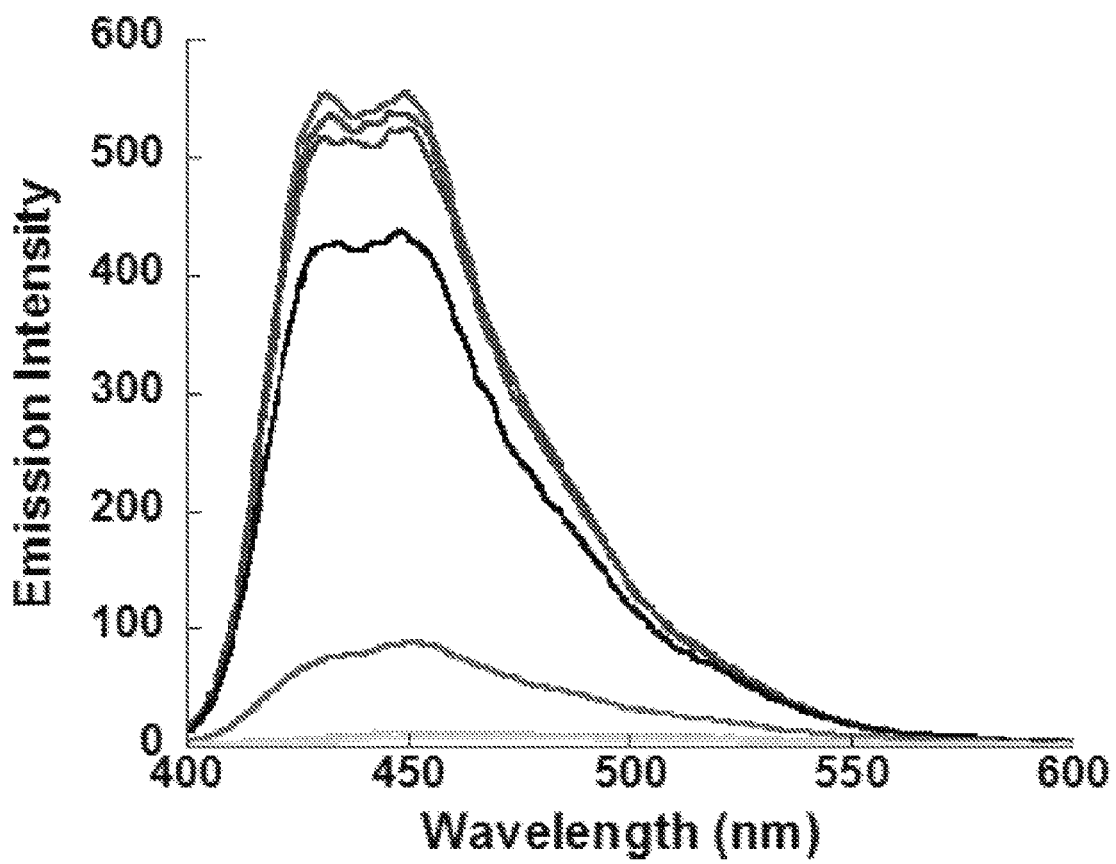
FIG. 3 is the fluorescence spectra of BPI-BP chloroform solution ($5 \times 10^{-6}$ mol/L) upon exposure to gamma radiation at various doses in accordance with an embodiment of the present invention.

A solution of BPI-BP in chloroform was prepared with a concentration of $5\times10^{-6}$ mol/L. The solution was exposed to levels of gamma radiation ranging from 0.1 Gy to 5 Gy. FIG. 3 shows the fluorescent spectrum of the solution at each level of gamma radiation. The original spectrum without any gamma radiation is the uppermost peak on the graph, with peaks around 430 and 460 nm in Wavelength (x-axis) corresponding to about 560 in Emission Intensity (y-axis). The next spectrum below, peaking around 540 in Emission Intensity (y-axis) is the spectrum after 0.1 Gy radiation. The other spectra peak lower and lower on the Emission Intensity scale until by the time 5 Gy was reached, the total Emission Intensity is almost zero. This experiment shows a measurable change in fluorescence of BPI-BP in chloroform at 0.1 Gy.

Figure 4:
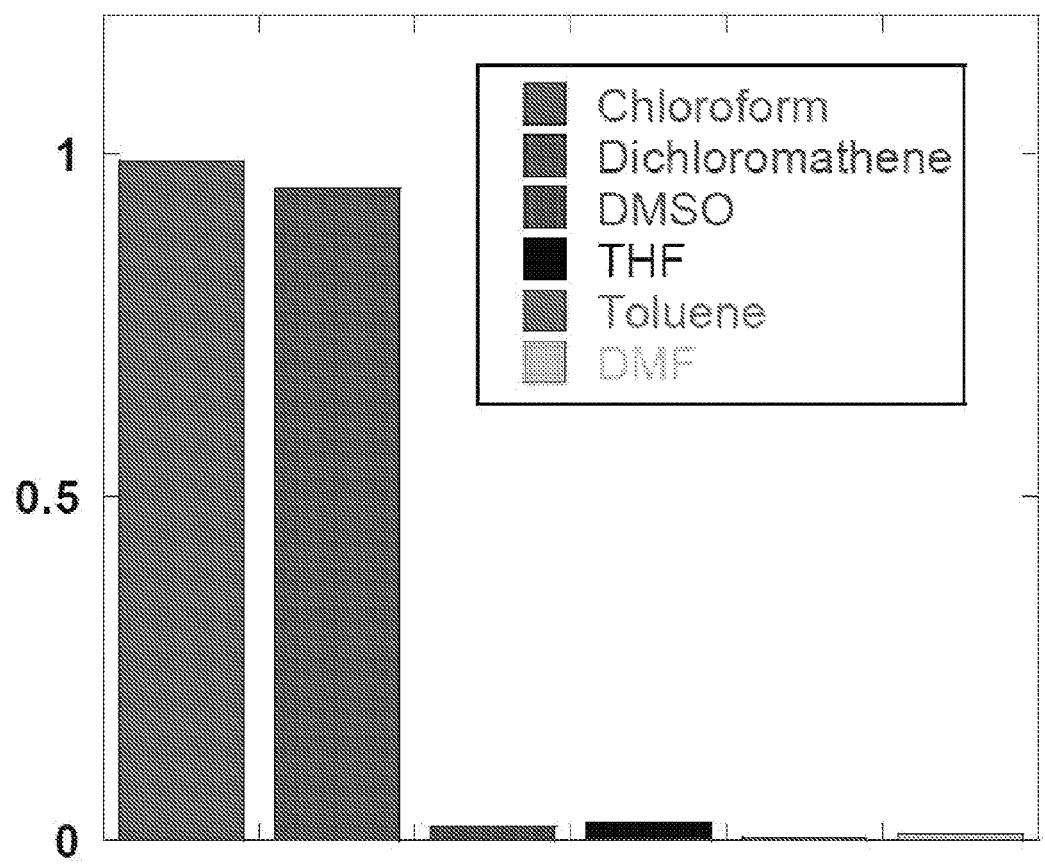
FIG. 4 is a bar graph of fluorescence quench efficiency of BPI-BP ($5 \times 10^{-6}$ mol/L) in solution with various solvents in accordance with an embodiment of the present invention.

FIG. 4 shows a comparison of quench efficiency (y-axis) for BPI-BP in various solvents. Each solution had a concentration of $5\times10^6$ mol/L. Each solution was exposed to 4.0 Gy of gamma radiation, and then the quench efficiency was measured. The solvents tested were, from left to right on the bar graph: chloroform, dichloromethane, DMSO, THF, toluene, and DMF. As shown on the graph, chloroform and dichloromethane provided a much higher quench efficiency than any of the other solvents. This experiment demonstrates that solutions of BPI-BP in halogen solvents can be effective at detecting gamma radiation by quenching fluorescence of the BPI-BP.

Figure 5:
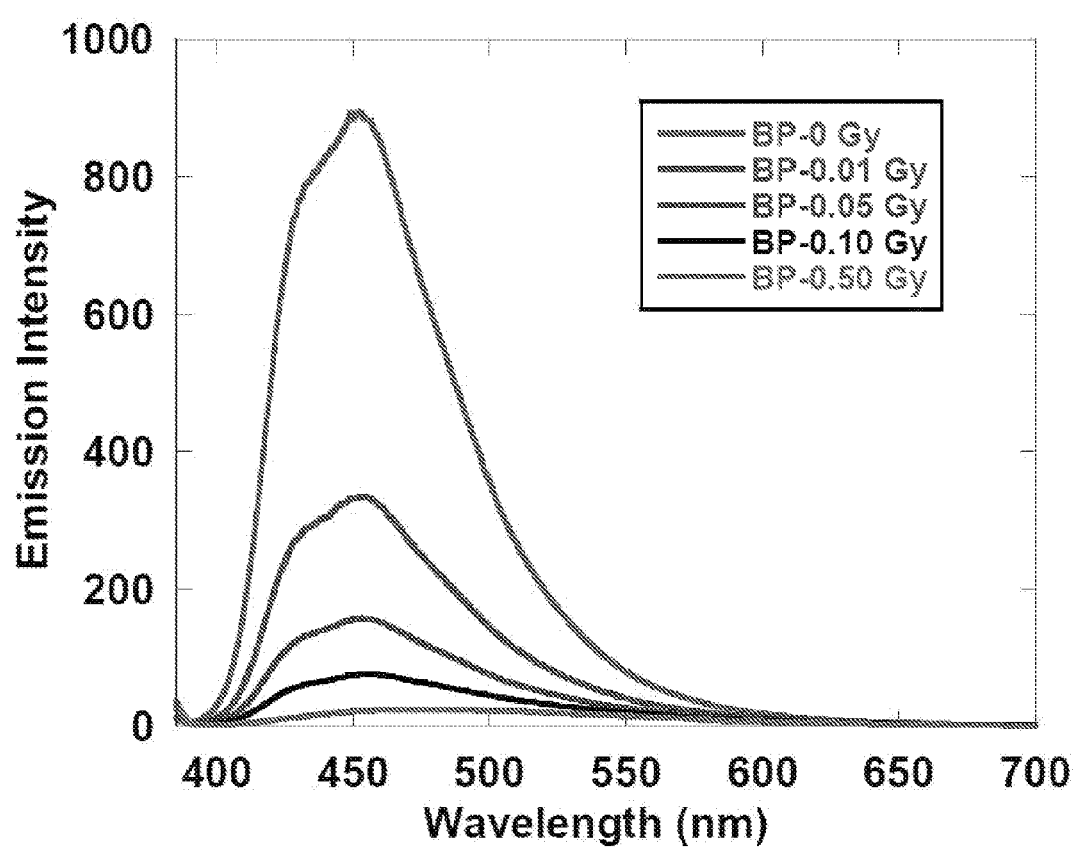
FIG. 5 is the fluorescence spectra of BPI-BP dichloromethane solution ($5 \times 10^{-6}$ mol/L) with benzil added upon exposure to gamma radiation at various doses in accordance with an embodiment of the present invention.

FIG. 5 shows emission spectra of a solution of BPI-BP in dichloromethane with benzil added. The concentration of BPI-BP was $5\times10^{-6}$ mol/L. The solution was exposed to levels of gamma radiation ranging from 0 Gy to 0.50 Gy. The original spectrum without any gamma radiation exposure is the uppermost peak on the graph, peaking around 900 in Emission Intensity (y-axis) and 450 nm Wavelength (x-axis). The second peak down is the spectrum after exposure to 0.01 Gy, peaking around 350 in Emission Intensity. This experiment shows that the addition of benzil, an initiator, dramatically increased the sensitivity of the BPI-BP dichloromethane solution, so that gamma radiation at levels of 0.01 Gy were readily detectable.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. A sensor for detecting gamma radiation, the sensor comprising:
   a conjugated imidazole having the following structure:

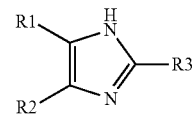

where at least one of R1, R2, and R3 are conjugated organic groups and wherein the conjugated imidazole has a nanofiber morphology, is present in a porous hydrophilic material, or has both the nanofiber morphology and is present in the porous hydrophilic material;
   a radical generating component, wherein the conjugated imidazole is capable of reacting with a radical or ion formed by a reaction of the gamma radiation with the radical generating component to decrease a molar extinction coefficient of the conjugated imidazole or to quench fluorescence of the conjugated imidazole; and
   a radiation detection indicator operatively associated with the conjugated imidazole configured to indicate a decrease in the molar extinction coefficient of the conjugated imidazole or a quenching of fluorescence of the conjugated imidazole.

2. The sensor of claim 1, wherein each of R1, R2, and R3 are conjugated organic groups.

3. The sensor of claim 2, wherein R1, R2, and R3 are independently selected from the group consisting of vinyl, 1,3-butadienyl, ethynyl, carbonyl,

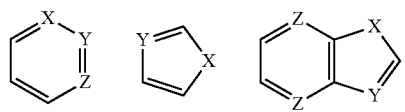

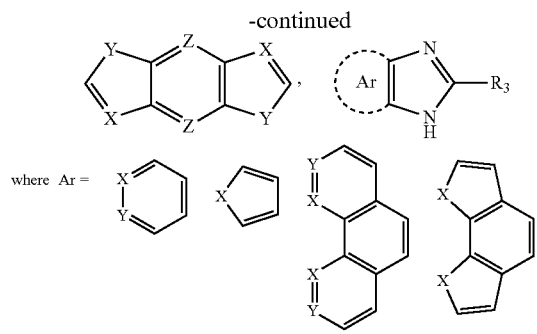

and where X, Y, and Z are independently selected from C, N, S, O, Si, and P; naphthalene, phenanthrene, and combinations thereof.

4. The sensor of claim 1, wherein R3 comprises a substituted imidazole group and a bridge group, such that the conjugated imidazole has the following structure:

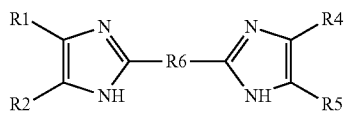

where R4, R5, and R6 are conjugated organic groups.

5. The sensor of claim 4, wherein R4, R5, and R6 are independently selected from the group consisting of vinyl, 1,3-butadienyl, ethynyl, carbonyl,

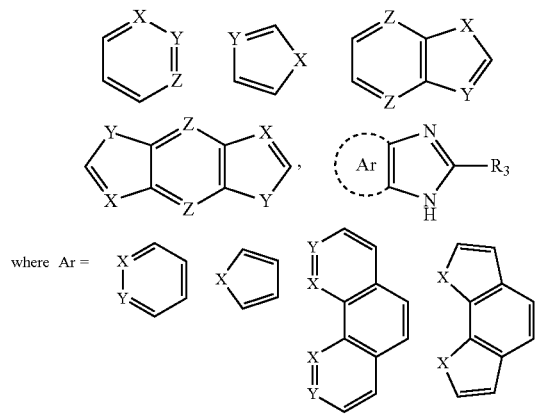

and where X, Y, and Z are independently selected from C, N, S, O, Si, and P; naphthalene, phenanthrene, and combinations thereof.

6. The sensor of claim 1, wherein R3 comprises triphenylamine such that the conjugated imidazole has the following structure:

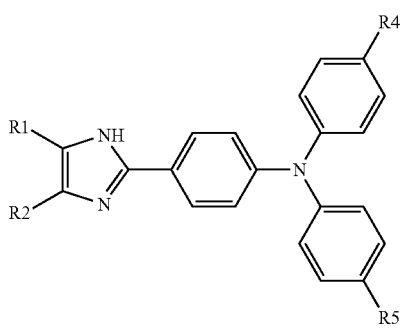

where R4 and R5 are conjugated organic groups or hydrogen.

7. The sensor of claim 1, wherein the conjugated imidazole is selected from the group consisting of 4,4'-Bis(1H-phenanthro[9,10-d]imidazol-2-yl)phenyl ("BPI-Ph"); 4,4'-Bis(1H-phenanthro[9,10-d]imidazol-2-yl)biphenyl ("BPI-BP"); 1,4-bis(4,5-diphenyl-1H-imidazol-2-yl)benzene (BDPI-Ph); 4,4'-bis(4,5-diphenyl-1H-imidazol-2-yl)biphenyl (BDPI-BP); 2,2'-(9,9-bis(2-ethylhexyl)-9H-fluorene-2,7-diyl)bis(1H-phenanthro[9,10-d]imidazole) (BPI-Flu); 2,2'-(9-(2-ethylhexyl)-9H-carbazole-2,7-diyl)bis(1H-phenanthro[9,10-d]imidazole) (BPI-Cb); tris(4-(1H-phenanthro[9,10-d]imidazol-2-yl)phenyl)amine (PI-TPA); 2-phenyl-1H-phenanthro[9,10-d]imidazole (PI-Ph); 2,4,5-triphenyl-1H-imidazole (TPI); 4-(1H-phenanthro[9,10-d]imidazol-2-yl)-N,N-diphenylaniline (PI-DPA); N,N-dimethyl-4-(1H-phenanthro[9,10-d]imidazol-2-yl)aniline (PI-DMA); and combinations thereof.

8. The sensor of claim 1, wherein the radical generating component comprises a halogen solvent.

9. The sensor of claim 8, wherein the conjugated imidazole is solvated in the halogen solvent.

10. The sensor of claim 1, wherein the radical generating component comprises a radical generating polymer.

11. The sensor of claim 10, wherein the radical generating polymer is selected from the group consisting of polymethyl-methacrylate, polyolefinsulfone, polypropylene, 2-methyl nylon-3, and mixtures thereof.

12. The sensor of claim 1, wherein the conjugated imidazole is present as the porous hydrophilic material and the porous hydrophilic material is at least one of a thin film, a cellulose fibril material, and a nanofiber surface-modified with the conjugated imidazole.

13. The sensor of claim 1, wherein the radical generating component comprises an organic molecule modified with a high-Z element.

14. The sensor of claim 13, wherein the organic molecule modified with a high Z-element is selected from the group consisting of triphenylbismuth, diiodobenzene, and mixtures thereof.

15. The sensor of claim 1, further comprising a radical initiator.

16. The sensor of claim 15, wherein the radical initiator is selected from the group consisting of benzil, benzyl bromide, benzoyl peroxide, azobisisobutyronitrile, tert-butyl hydroperoxide, cyclohexanone peroxide, 1,1'-azobis(cyclohexanecarbonitrile), acetone peroxide, 4,4'-azobis(4-cyanopentanoic acid), azobisisobutyronitrile, benzoyl peroxide, di-tert-butyl peroxide, methyl ethyl ketone peroxide, potassium persulfate, tributyltin hydride, and mixtures thereof.

17. The sensor of claim 1, wherein the sensor has a lower detection limit between about 0.01 Gy and about 1 Gy.

18. The sensor of claim 1, wherein the radiation detection indicator comprises a colorimetric detector operatively associated with the conjugated imidazole configured to measure a color change of the conjugated imidazole.

19. The sensor of claim 1, further comprising an ultraviolet light source operatively associated with the conjugated imidazole configured to excite the conjugated imidazole to fluorescence.

20. The sensor of claim 19, wherein the radiation detection indicator comprises a fluorimeter operatively associated with the conjugated imidazole configured to measure a fluorescence change of the conjugated imidazole.

21. A method for detecting gamma radiation, comprising
placing the conjugated imidazole and the radical generating component of claim 1 in an area having gamma radiation; and identifying a color change associated with the decrease of the molar extinction coefficient or with the quench of the fluorescence.

22. The method of claim 21, wherein identifying the color change is by visual inspection.

23. The method of claim 21, wherein identifying the color change is by an electronic device.

24. The method of claim 21, wherein the method has a lower detection limit between about 0.01 Gy and about 1 Gy.

25. The method of claim 21, wherein the conjugated imidazole is provided in a three-dimensional material and the color change forms a three-dimensional map of gamma radiation dosage.

26. A sensor for detecting gamma radiation, the sensor comprising:
   a conjugated imidazole having the following structure:

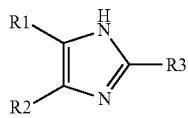

where at least one of R1, R2, and R3 are conjugated organic groups such that:
   a) R1, R2, and R3 are independently selected from the group consisting of vinyl, 1,3-butadienyl, ethynyl, carbonyl,

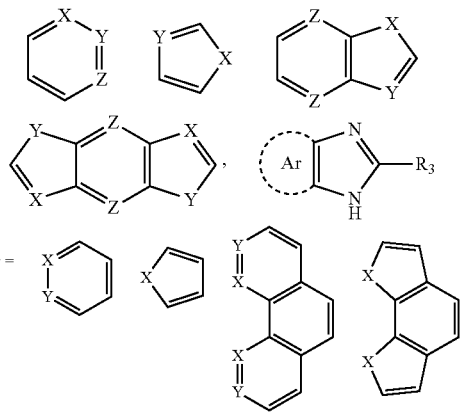

and where X, Y, and Z are independently selected from C, N, S, O, Si, and P; naphthalene, phenanthrene, and combinations thereof;
   b) R3 comprises a substituted imidazole group and a bridge group, such that the conjugated imidazole has the following structure:

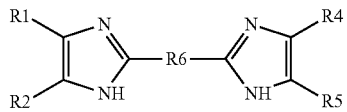

where R4, R5, and R6 are conjugated organic groups;
   c) R3 comprises triphenylamine such that the conjugated imidazole has the following structure:

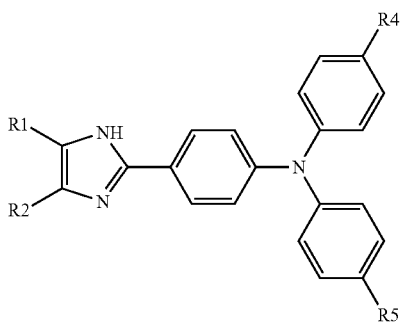

where R4 and R5 are conjugated organic groups or hydrogen; or
   d) the conjugated imidazole is selected from the group consisting of 4,4'-Bis(1H-phenanthro[9,10-d]imidazol-2-yl)phenyl ("BPI-Ph"); 4,4'-Bis(1H-phenanthro[9,10-d]imidazol-2-yl)biphenyl ("BPI-BP"); 1,4-bis(4,5-diphenyl-1H-imidazol-2-yl)benzene (BDPI-Ph); 4,4'-bis(4,5-diphenyl-1H-imidazol-2-yl)biphenyl (BDPI-BP); 2,2'-(9,9-bis(2-ethylhexyl)-9H-fluorene-2,7-diyl)bis(1H-phenanthro[9,10-d]imidazole) (BPI-Flu); 2,2'-(9-(2-ethylhexyl)-9H-carbazole-2,7-diyl)bis(1H-phenanthro[9,10-d]imidazole) (BPI-Cb); tris(4-(1H-phenanthro[9,10-d]imidazol-2-yl)phenyl)amine (PI-TPA); 2-phenyl-1H-phenanthro[9,10-d]imidazole (PI-Ph); 2,4,5-triphenyl-1H-imidazole (TPI); 4-(1H-phenanthro[9,10-d]imidazol-2-yl)-N,N-diphenylaniline (PI-DPA); N,N-dimethyl-4-(1H-phenanthro[9,10-d]imidazol-2-yl)aniline (PI-DMA); and combinations thereof; and
   a radical generating component, wherein the conjugated imidazole is capable of reacting with a radical or ion formed by a reaction of the gamma radiation with the radical generating component to decrease a molar extinction coefficient of the conjugated imidazole or to quench fluorescence of the conjugated imidazole; and
   a radiation detection indicator operatively associated with the conjugated imidazole configured to indicate a decrease in the molar extinction coefficient of the conjugated imidazole or a quenching of fluorescence of the conjugated imidazole.

27. The sensor of claim 26, wherein R4, R5, and R6 are independently selected from the group consisting of vinyl, 1,3-butadienyl, ethynyl, carbonyl,

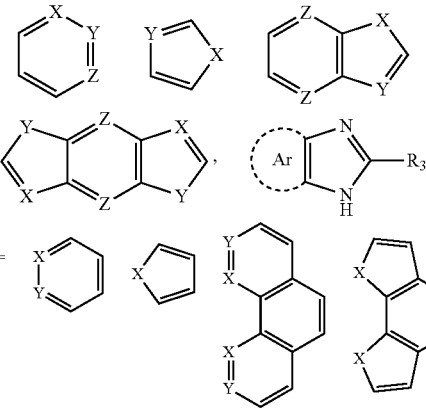

and where X, Y, and Z are independently selected from C, N, S, O, Si, and P; naphthalene, phenanthrene, and combinations thereof.

* * * * *